United States Patent
Toyokawa et al.

(10) Patent No.: US 10,278,843 B2
(45) Date of Patent: May 7, 2019

(54) STENT

(71) Applicant: PIOLAX MEDICAL DEVICES, INC., Yokohama-shi (JP)

(72) Inventors: Yoshihide Toyokawa, Yokohama (JP); Kyosuke Shirakawa, Yokohama (JP)

(73) Assignee: PIOLAX MEDICAL DEVICES, INC., Yokohama-Shi, Kanagawa (JP)

( * ) Notice: Subject to any disclaimer, the term of this patent is extended or adjusted under 35 U.S.C. 154(b) by 6 days.

(21) Appl. No.: 15/550,448

(22) PCT Filed: Feb. 8, 2016

(86) PCT No.: PCT/JP2016/053647
§ 371 (c)(1),
(2) Date: Aug. 11, 2017

(87) PCT Pub. No.: WO2016/129551
PCT Pub. Date: Aug. 18, 2016

(65) Prior Publication Data
US 2018/0028337 A1 Feb. 1, 2018

(30) Foreign Application Priority Data

Feb. 13, 2015 (JP) ................. 2015-026313

(51) Int. Cl.
| A61F 2/915 | (2013.01) |
| A61F 2/07 | (2013.01) |
| A61F 2/958 | (2013.01) |
| A61F 2/82 | (2013.01) |

(52) U.S. Cl.
CPC ................ *A61F 2/915* (2013.01); *A61F 2/07* (2013.01); *A61F 2/958* (2013.01); *A61F 2002/072* (2013.01); *A61F 2002/825* (2013.01); *A61F 2002/91541* (2013.01); *A61F 2002/91575* (2013.01)

(58) Field of Classification Search
CPC .. A61F 2/915; A61F 2/07; A61F 2/958; A61F 2002/91575; A61F 2002/91583
See application file for complete search history.

(56) References Cited

U.S. PATENT DOCUMENTS

| 2004/0093073 A1 | 5/2004 | Lowe et al. |
| 2004/0111147 A1 | 6/2004 | Rabkin et al. |
| 2012/0296362 A1 | 11/2012 | Cam et al. |
| 2013/0317595 A1 | 11/2013 | Obradovic et al. |

FOREIGN PATENT DOCUMENTS

| JP | 2005-524488 A | 8/2005 |
| JP | 2007-529245 A | 10/2007 |
| JP | 2014-503276 A | 2/2014 |

OTHER PUBLICATIONS

International Search Report (ISR) (PCT Form PCT/ISA/210), in PCT/JP2016/053647, dated Apr. 5, 2016.

*Primary Examiner* — William H Matthews
(74) *Attorney, Agent, or Firm* — McGinn I.P. Law, Group, PLLC.

(57) ABSTRACT

A stent has strut parts bent in a zigzag shape, connected at both ends thereof, and formed in a ring shape, and bridge parts for connecting the strut parts in an axial direction, peak parts of strut parts excluding a strut part at the lead toward one end are all connected by bridge parts and clustered a plurality thereof at a time by the bridge parts, and connected to valley parts of struts adjacent toward the one end of the stent, and each strut part includes valley parts which are not connected to a bridge part.

10 Claims, 13 Drawing Sheets

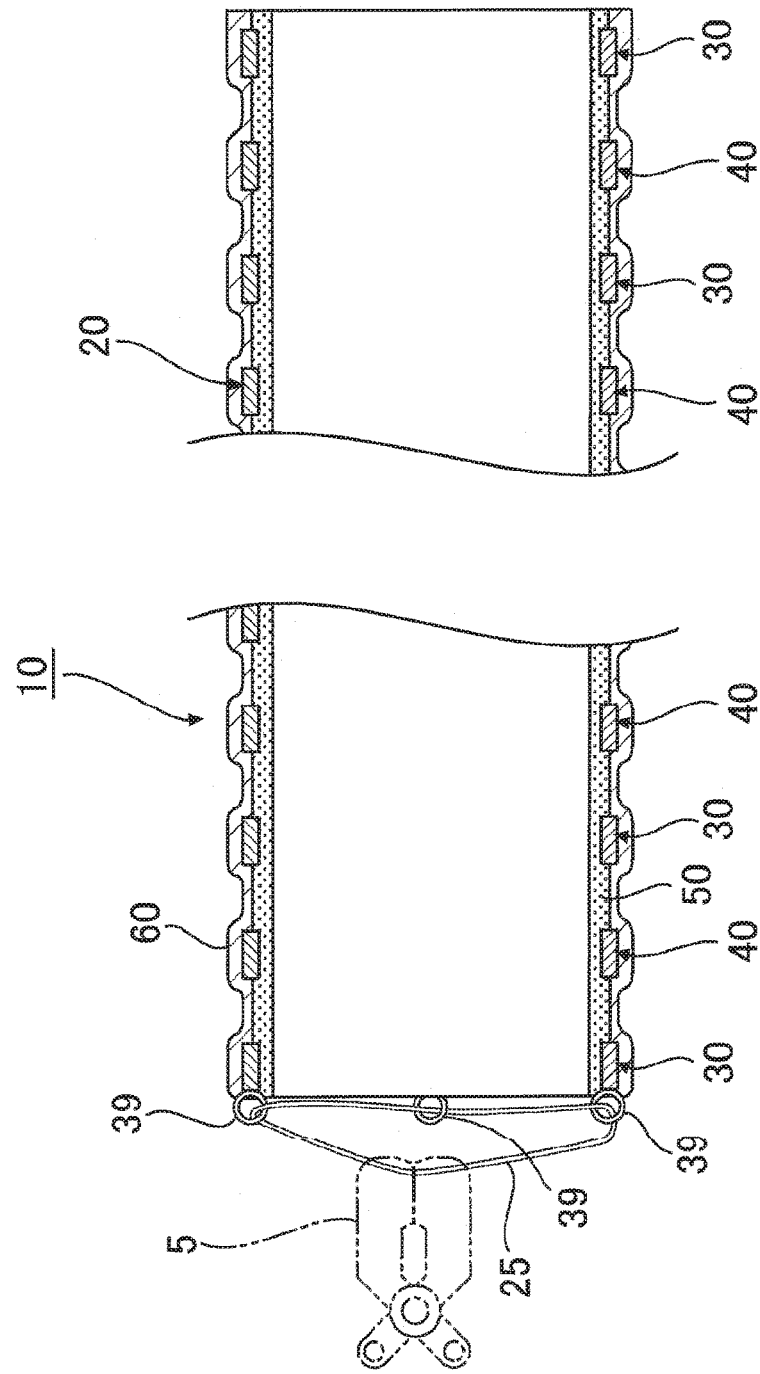

STENT

TECHNICAL FIELD

The present invention relates to a stent which is to be indwelled in, for example, a tubular organ such as the bile duct, the ureter, the trachea, or the blood vessel, a body cavity, or another body tissue.

BACKGROUND ART

Conventionally, treatment using a stent is performed in which, for example, the stent is indwelled in a stenosed or obstructed portion formed in the body, for example, a tubular organ such as the bile duct, the ureter, the trachea, the blood vessel, or the esophagus, or a body cavity, and the stenosed or obstructed portion is expanded, thereby allowing the bile, the blood, or the like to easily flow, or the stent is indwelled in a portion where an aneurysm occurs, to prevent rupture of the aneurysm from occurring.

In the case where a stent is indwelled in a tubular organ such as the bile duct, with the elapse of time, the inner cavity of the stent may be sometimes closed by body fluid such as the bile, or growth of cancer cells, and a situation in which the stent must be recovered from the body may occur. When such a situation occurs, for example, one end portion of the stent indwelled in the tubular organ is gripped by forceps, a snare, or the like, and then pulled, thereby tearing the stent from the inner wall of the tubular organ, and thereafter the stent is further pulled so as to be extracted from the tubular organ.

As a stent which can be removed from the body, for example, Patent Literature 1 below discloses a stent which has plural annular segments that are formed by bending plural segment struts in a zigzag pattern via mountain- or valley-shaped transition sections, and in which adjacent annular segments are axially coupled to each other via plural connector struts. An eyelet-like head end is disposed in each of mountain-shaped bent portions of the annular segments positioned in one end portion of the stent. When the head end is gripped and pulled, or when a thread or the like is passed through the plural head ends, and the thread is pulled, the stent can be pulled out from the body. Moreover, the mountain-shaped transition sections which are disposed in adjacent annular segments, and which are directed toward the head ends are coupled to each other by the connector struts (see FIG. 1 and amended paragraph [0020]).

CITATION LIST

Patent Literature

Patent Literature 1: JP-T-2007-529245

SUMMARY OF INVENTION

Technical Problem

In the case where a stent is indwelled in a tubular organ which largely bends, such as the bile duct, also the stent is indwelled in a bent state, and therefore a stent is requested to have a flexibility and a kink resistance (characteristics in which, even when the stent is bent, breaking hardly occurs, and the inner cavity is hardly closed). Also in the case where, after a stent is indwelled, cancer cells or the like grow in a tubular organ, there is a case where the stent is compressed and bent by the grown cancer cells or the like. Also in this case, a stent is requested to have the flexibility and kink resistance which have been described above.

In the stent disclosed in Patent Literature 1 above, however, all of the mountain-shaped transition sections of predetermined annular segments, and all of the mountain-shaped transition sections of adjacent other annular segments are coupled together by the connector struts, and therefore there is a disadvantage that the number of the connector struts is large, and, when the stent is bent, the bending is hardly performed, and a kink easily occurs (the stent is easily broken, and the inner cavity is easily closed).

Therefore, it is an object of the invention to provide a stent which, in the case where the stent is indwelled in the body, can be smoothly extracted from the body, and which exhibits an excellent flexibility and an excellent kink resistance.

Solution to Problem

To attain the object, the invention provides
a stent including:
plural strut portions each of which is
formed to be bent in a zigzag manner and coupled at both ends to have an annular shape, or
formed by coupling together plural frame-like members having a predetermined bent shape, in juxtaposition in a circumferential direction; and
bridge portions which couple together the plural strut portions in an axial direction,
wherein each strut portion includes:
mountain portions which correspond to bent portions that are projected toward one end side of the stent; and
valley portions which correspond to bent portions that are projected toward another end side,
wherein all the mountain portions of each strut portion other than the strut portion which is positioned in a top on the one end side are coupled to the bridge portions, such that the mountain portions are bundled into groups of the plural mountain portions by the bridge portions, and coupled to the valley portions or the mountain portions of another strut portion which is adjacent on the one end side, and
wherein a part of the valley portions of each strut portion is not coupled to the bridge portions.
There may be provided
the stent,
wherein the mountain portions of each strut portion other than the strut portion which is positioned in the top on the one end side are bundled into groups of the 3 or 4 mountain portions by the bridge portions, and coupled to the valley portions or the mountain portions of the another strut portion which is adjacent on the one end side.
There may be provided
the stent,
wherein the bridge portions, which are coupled to the mountain portions of each strut portion other than the strut portion which is positioned in the top on the one end side, are also coupled to the valley portions of the another strut portion which is adjacent on the one end side.
There may be provided
the stent,
wherein the bridge portions, which are coupled to the mountain portions of each strut portion other than the strut portion which is positioned in the top on the one end side, is each bundled such that the plural mountain portions are bundled into a bundled portion at a middle position on a way, and wherein the bundled portion is coupled to the valley portion or the mountain portion of the another strut portion which is adjacent on the one end side.

There may be provided the stent, wherein the valley portions or the mountain portions of each strut portion include a constant number of the valley portions or the mountain portions which are not coupled to the bridge portions in the circumferential direction between the valley portions or the mountain portions which are coupled to the bridge portions.

There may be provided the stent, wherein, with each strut portion other than the strut portion which is positioned in the top on the one end side, the 3 to 6 bridge portions are disposed in the circumferential direction, the bridge portion bundling the plural mountain portions and being coupled to the valley portion or the mountain portion of the another strut portion which is adjacent on the one end side.

There may be provided the stent, wherein the bridge portions, which are coupled to the mountain portions of each strut portion other than the strut portion which is positioned in the top on the one end side, is each bundled such that the 3 or more mountain portions coupled at the other end side are sequentially bundled at respective middle positions on a way toward the one end side while being shifted from one another in the axial direction into a bundled portion, and wherein the bundled portion is coupled to the valley portion or the mountain portion of the another strut portion which is adjacent on the one end side.

Advantageous Effects of Invention

According to the invention, when the stent is inserted from the other end side and indwelled in the body, for example, a tubular organ such as the bile duct, or a body cavity, and required to be recovered, the one end side of the stent is gripped and pulled by forceps, a snare, or the like, whereby all of the mountain portions of the strut portions other than the strut portion which is positioned in the top on the one end side are pulled via the bridge portions, and the mountain portions are easily converged to reduce the diameter. While causing the mountain portions to be hardly caught by the inner wall of the tubular organ or the body cavity, therefore, the stent can be smoothly extracted from the body.

A part of the valley portions of each strut portion is not coupled to the bridge portions. Therefore, the space surrounded by the strut portion and the bridge portions is widened, the flexibility of the stent is enhanced, and, when the stent is bent, the stent hardly kinks.

BRIEF DESCRIPTION OF THE DRAWINGS

FIG. 1A is a perspective view of the stent main body constituting the stent. FIG. 1B is a perspective view of a state where the stent main body is covered by a cover.

FIG. 2 is a sectional view of the stent.

MODE FOR CARRYING OUT THE INVENTION

Hereinafter, a first embodiment of the stent of the invention will be described with reference to FIGS. 1A to 9.

Figure 1A:
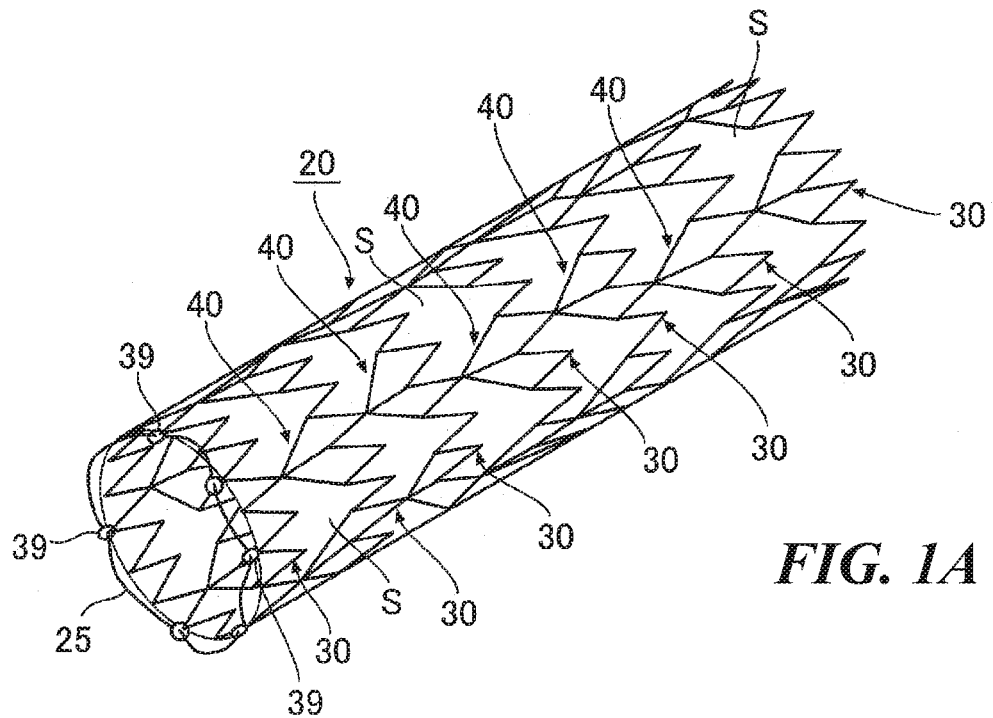
FIGS. 1A and 1B show a first embodiment of the stent of the invention.
Figure 1B:
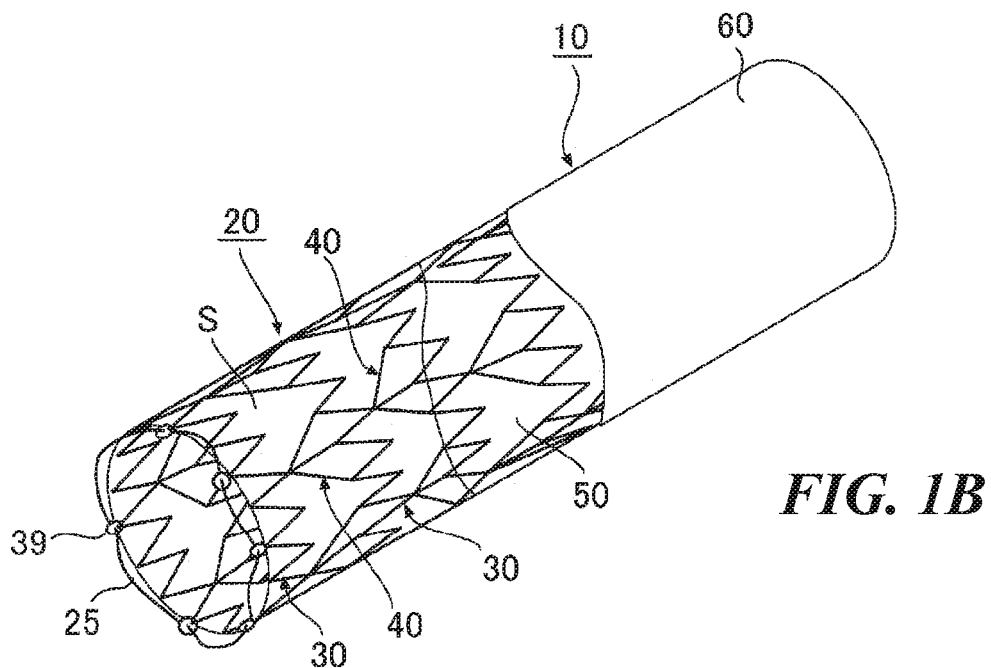

As shown in FIG. 1A, a stent 10 of the embodiment is a so-called covered stent having a structure where the stent has a stent main body 20 in which the both ends are opened, and which has a substantially cylindrical shape, as shown in FIG. 1B, an inner cover 50 covers the inside of the stent main body 20, and an outer cover 60 covers the outside of the stent main body 20. Of course, the stent may be a stent in which the stent main body is not covered by the inner cover 50 and the outer cover 60, or that in which the stent main body is covered by only one of the covers.

Figure 3:
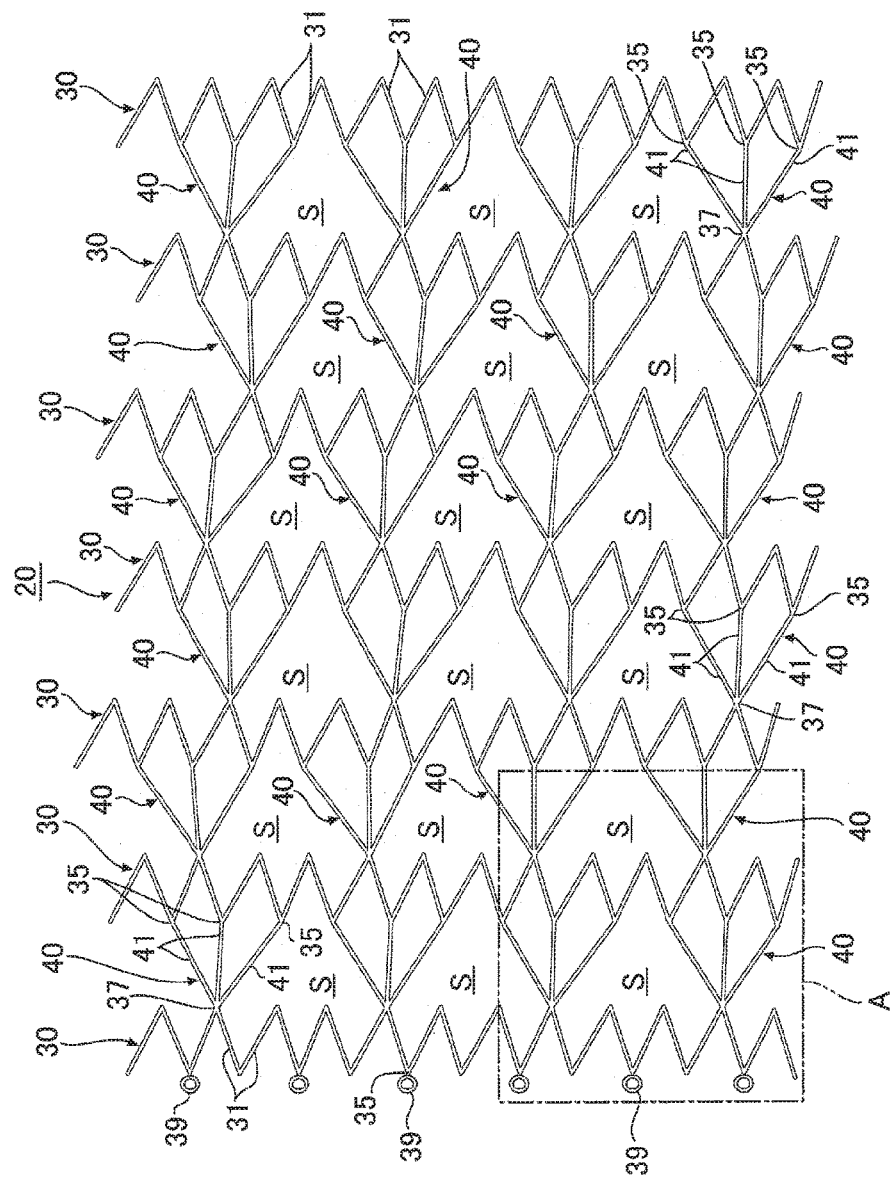
FIG. 3 is a development view of the stent main body constituting the stent.

Referring also to the development view of FIG. 3, the stent main body 20 has plural strut portions 30 in each of which a frame 31 is bent in a zigzag manner so as to form mountain portions 35 and valley portions 37, and formed into annular shape by coupling the both ends of the frame to each other. These plural strut portions 30 are coupled together in the axial direction of the stent 10 via bridge portions 40, thereby constituting the stent main body 20.

Each of the strut portions may have a structure that is formed into an annular shape by coupling plural frame-like members having a predetermined bent shape, together side by side in the circumferential direction of the stent, in place of the structure that is formed into an annular shape by bending the strut portion in a zigzag pattern, and coupling the both ends to each other. The structure in which each of the strut portions forms "frame-like member" will be described in a second embodiment which will be described later (see FIG. 10).

In the strut portions 30, preferably, 8 to 24 V-shape bent portions 32 (the portion enclosed by the dash-dot line in FIG. 4) in each of which adjacent frames 31, 31 are formed into a V-like shape are disposed in each strut portion 30 in the circumferential direction of the strut portion, and more preferably 12 to 16 V-shape bent portions are disposed.

In the following description, the bent portions which are projected toward one end side (the left side in FIGS. 3 and 4, hereinafter referred to merely as "the one end side") in the axial direction of the strut portions 30 are referred to as mountain portions 35, and those which are projected toward the other end side (the right side in FIGS. 3 and 4, hereinafter referred to merely as "the other end side") in the axial direction are referred to as valley portions 37.

Figure 5:
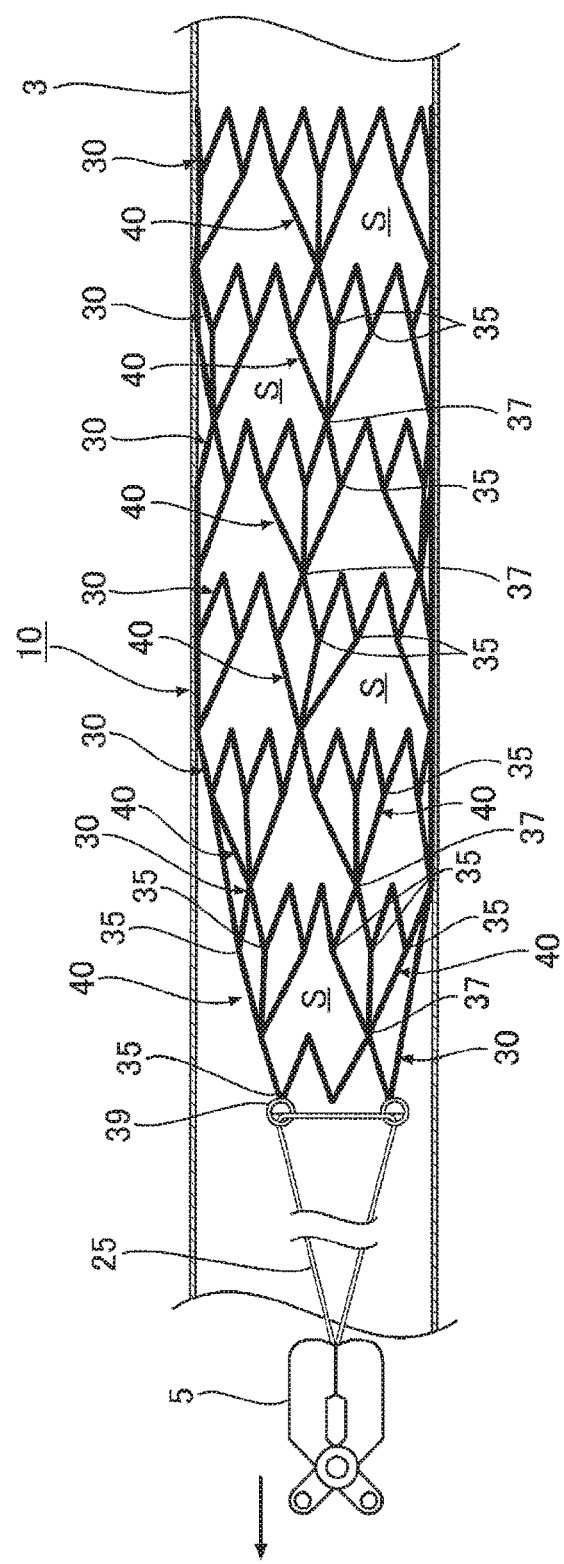
FIG. 5 is an enlarged diagram showing a state where the stent is pulled out from the body.

As shown in FIG. 3, in the mountain portions 35 of the strut portion 30 which is positioned in the top on the one end side of the stent 10, pull-out portions 39 having a ring-like shape are alternately disposed. A pull-out wire 25 having a loop-like shape is passed through the plural pull-out portions 39. As shown in FIG. 5, when the pull-out wire 25 is gripped and pulled by forceps 5 or the like, the stent 10 can be pulled out from the body. In FIG. 5, for the sake of convenience, only the stent main body 20 is shown.

The stent 10 is housed in a medical tube which is not shown, such as a catheter or a sheath, in a reduced-diameter state, and, when the stent is pushed out into the body from the tip end side of the medical tube, placed in position. In this case, the stent 10 is housed with directing the other end side where the valley portions 37 are disposed, in the pushing out direction, and inserted into the body from the other end side. When the stent 10 is to be recovered from the body, the stent is pulled out from one end side to which the mountain portions 35 are directed, and then housed in the medical tube.

Namely, "other end side of the stent" in the invention is an end portion in the insertion direction in the case where the stent is to be inserted into the body, and "one end side of the stent" is an end portion in the pull-out direction in the case where the stent is to be recovered from the body.

Alternatively, the pull-out portions 39 may be disposed in all of the mountain portions 35 of the strut portion 30 which is positioned in the top on the one end side of the stent 10.

Figure 4:
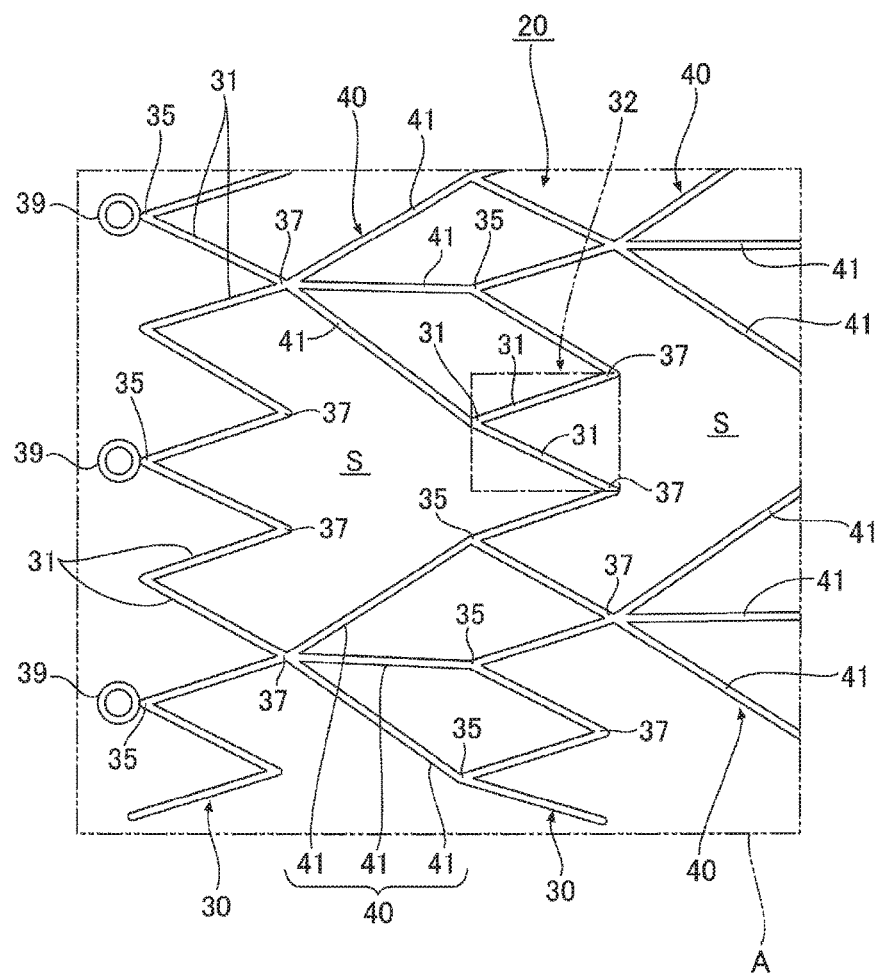
FIG. 4 is an enlarged view of the portion A in FIG. 3.

As shown in FIGS. 3 and 4, each group of plural (here, 3) mountain portions 35 of the strut portions 30 other than the strut portion 30 which is positioned in the top on the one end side of the stent 10 and which has the pull-out portions 39 are bundled by the bridge portions 40, and coupled to the valley portion 37 of the strut portion 30 which is adjacent on the one end side of the stent. The mountain portions 35 of the strut portions 30 other than the strut portion 30 which is positioned in the top on the one end side of the stent 10 and which has the pull-out portions 39 are coupled to the bridge portions 40, and the valley portions 37 of the strut portions 30 include those which are not coupled to the bridge portions 40.

The above-described structure will be described in detail with reference to FIGS. 3 and 4. Each bridge portion 40 in the embodiment has a structure where the bridge portion has 3 frames 41 in which their tip ends are coupled to one another, the basal ends of the frames 41 are coupled to the 3 mountain portions 35, 35, 35 of each strut portion 30 which are adjacent to one another in the circumferential direction of the stent, respectively, the 3 mountain portions 35 are bundled, and the tip end of the bridge portion 40 is coupled to one of the valley portions 37 of the strut portion 30 which is adjacent on the one end side of the stent.

When plural strut portions 30 are coupled via bridge portions 40 as described above, plural spaces S (see FIGS. 3 and 4) each of which is surrounded by strut portions 30, 30 that are adjacent to each other in the stent axial direction, and bridge portions 40, 40 that are adjacent to each other in the stent circumferential direction are formed in the stent main body 20.

As shown in FIG. 3, preferably, 3 to 6 bridge portions 40 are disposed in the circumferential direction of each strut portion 30, and more preferably 3 or 4 bridge portions are disposed.

As shown in FIG. 3, in the stent 10, the valley portions 37 of each strut portion 30 are arranged such that, a constant number of valley portions which are not coupled to the bridge portions 40 exist in the circumferential direction between valley portions which are coupled to the bridge portions 40.

In the embodiment, in each strut portion 30, 2 valley portions 37 which are not coupled to the bridge portions 40 exist between the valley portions 37 which are coupled to the bridge portions 40.

The number of valley portions 37 that are disposed between the valley portions 37 which are coupled to the bridge portions 40, and that are not coupled to the bridge portions 40 may be 1 or 3 or more. Preferably, the number is 1 to 3, and more preferably 1 or 2.

Figure 8:
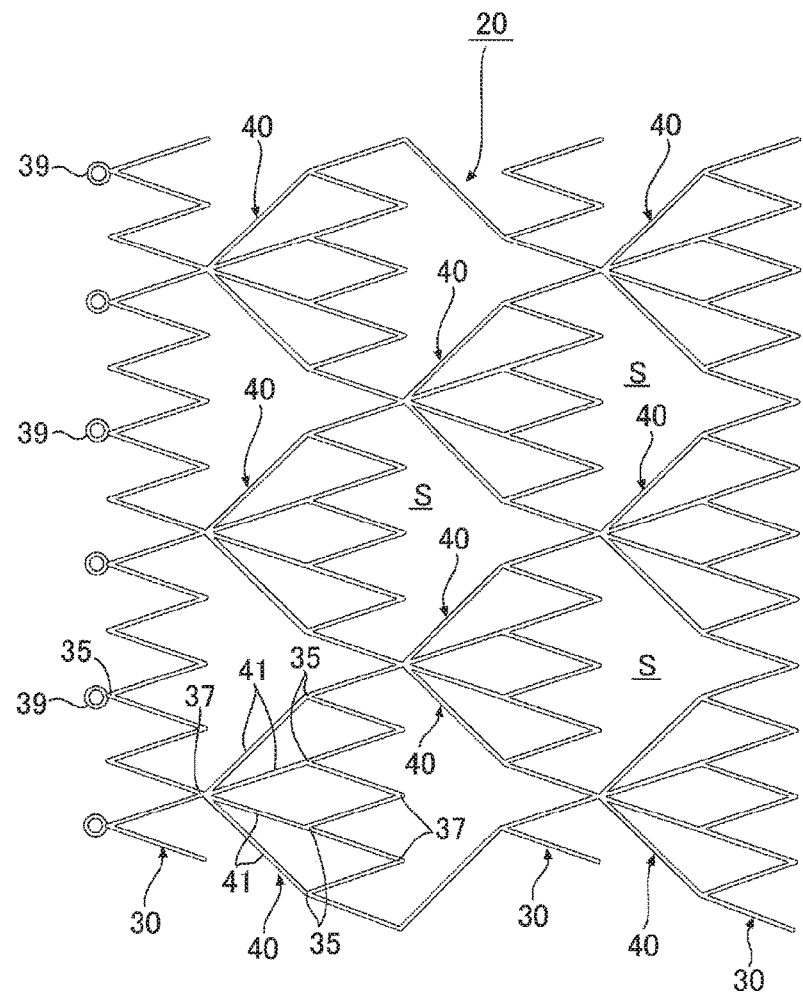
FIG. 8 is a development view showing a modification of the stent main body constituting the stent.

In the embodiment, the mountain portions 35 of the strut portions 30 other than the strut portion 30 which is positioned in the top on the one end side of the stent 10 and which has the pull-out portions 39 are bundled into groups of 3 mountain portions 35 by the bridge portions 40, respectively. The number of mountain portions 35 which are bundled by one bridge portion 40 is not particularly limited. As shown in FIG. 8, for example, each bridge portion 40 may be configured so as to have 4 frames 41, and the basal ends of the frames may be coupled to 4 mountain portions 35 which are adjacent to one another in the circumferential direction of each strut portion 30, respectively, so that the 4 mountain portions 35 are bundled.

Figure 9:
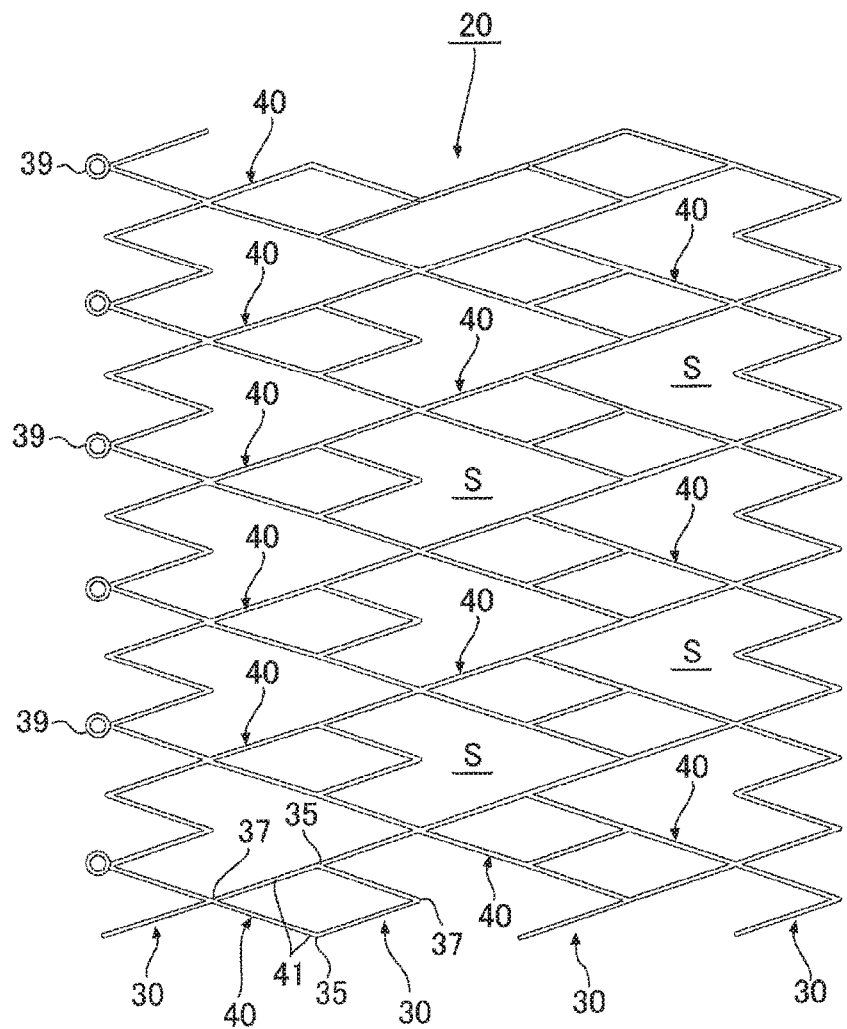
FIG. 9 is a development view showing another modification of the stent main body constituting the stent.

As shown in FIG. 9, alternatively, each bridge portion 40 may be configured so as to have 2 frames 41, and the basal ends may be coupled to 2 mountain portions 35 which are adjacent to one another in the circumferential direction of each strut portion 30, respectively, so that the 2 mountain portions 35 are bundled.

Although, in the embodiment, the tip ends of bridge portions 40 each of which bundles plural mountain portions 35 of each strut portion 30 are coupled to the valley portions 37 of the adjacent strut portion 30, respectively, the tip ends may be coupled to mountain portions 35. The structure in which the tip ends are coupled to mountain portions 35 will be described in a third embodiment (see FIG. 11) which will be described later.

The stent main body 20 in the embodiment is configured by processing a metal cylinder with laser processing, etching, or the like to form the pluralities of strut portions and bridge portions. Alternatively, for example, a metal plate is processed to dispose pluralities of strut portions and bridge portions which are in a zigzag pattern, or which are configured by frame-like members, and a stent main body is formed by bending the metal plate into a cylindrical shape.

The stent main body 20 is of the self-expandable type which is normally in the increased diameter state. Alternatively, the stent main body may be of the balloon expandable type in which the stent main body is previously attached to a balloon catheter or the like, and a balloon placed inside the stent is inflated, thereby expanding the stent main body.

The material of the stent main body 20 is not particularly limited, but, for example, stainless steel, Ta, Ti, Pt, Au, W, or a shape memory alloy such as a Ni—Ti alloy, a Co—Cr alloy, a Co—Cr—Ni alloy, a Cu—Zn—X (X=Al, Fe, or the like) alloy, a Ni—Ti—X (X=Fe, Cu, V, Co, or the like) alloy may be preferably used.

Furthermore, an X-ray marker which is made of, for example, Pt, Ti, Pd, Rh, Au, W, Ag, Bi, or Ta, an alloy of these metals, a synthetic resin containing powder of $BaSO_4$, Bi, W, or the like, or stainless steel, and which is X-ray opaque may be disposed at a predetermined position of the stent main body 20.

The outer diameter of the stent 10 is not particularly limited, and may be adequately set in accordance with the use. In an example case where the stent is used as a bile duct stent, preferably, the outer diameter is 4 to 20 mm, and more preferably 6 to 12 mm. Moreover, the widths of the strut portions 30 and bridge portions 40 which constitute the stent main body 20 are not particularly limited, but preferably 0.05 to 0.4 μm, and more preferably 0.1 to 0.3 μm. Furthermore, the thicknesses of the strut portions 30 and bridge portions 40 which constitute the stent main body 20 are not particularly limited, but preferably 0.05 to 0.4 μm, and more preferably 0.1 to 0.3 μm.

As described above, moreover, the inner cover 50 covers the inside of the stent main body 20, and the outer cover 60 covers the outside. As shown in the sectional view of FIG. 2, the inside of the stent main body 20 is covered by the inner cover 50, and its portion extending to a middle position in the thickness direction is buried in the inner cover. The outside of the stent main body 20 is covered by the outer cover 60, and its portion which is not buried in the inner cover 50 is buried in the outer cover. Mesh openings (air spaces defined by the plural frames 31 of the strut portions 30, and the plural frames 41 of the bridge portions 40) of the stent main body 20 are closed by the covers 50, 60.

Preferably, the inner cover 50 and the outer cover 60 are made of, for example, polyurethane, silicone, natural rubber, nylon elastomer, polyether block amide, polyethylene, polyvinyl chloride, polyvinyl acetate, a fluorine resin such as polytetrafluoroethylene (PTFE), perfluoroalkoxy resin (PFA), tetra-fluoroethylene/hexa-fluoropropylene copolymer (FEP), or ethylene-tetra-fluoroethylene copolymer (ETFE), olefin rubber such as polybutadiene, or styrene elastomer.

In the embodiment, the term "strut portions other than the strut portion which is positioned in the top on the one end side" in the invention indicates all strut portions 30 other than the strut portion 30 which has the pull-out portions 39, the term "strut portions" in the invention indicates all the strut portions 30 including the strut portion 30 which has the pull-out portions 39, and the term "the strut portions which are adjacent on the one end side" in the invention indicates a predetermined strut portion 30 which is adjacent to a certain predetermined strut portion 30 (in FIG. 3, for example, the term indicates the strut portion 30 which is adjacent to the strut portion 30 that is in the right end (on the side of the axial other end) of the sheet, and which is the second strut portion at the right end of the sheet). This is similarly applicable to embodiments which will be described later.

Next, an example of a method of using the stent 10 of the invention having the above-described configuration will be described. The use method is a mere example, and not particularly limited.

Figure 6:
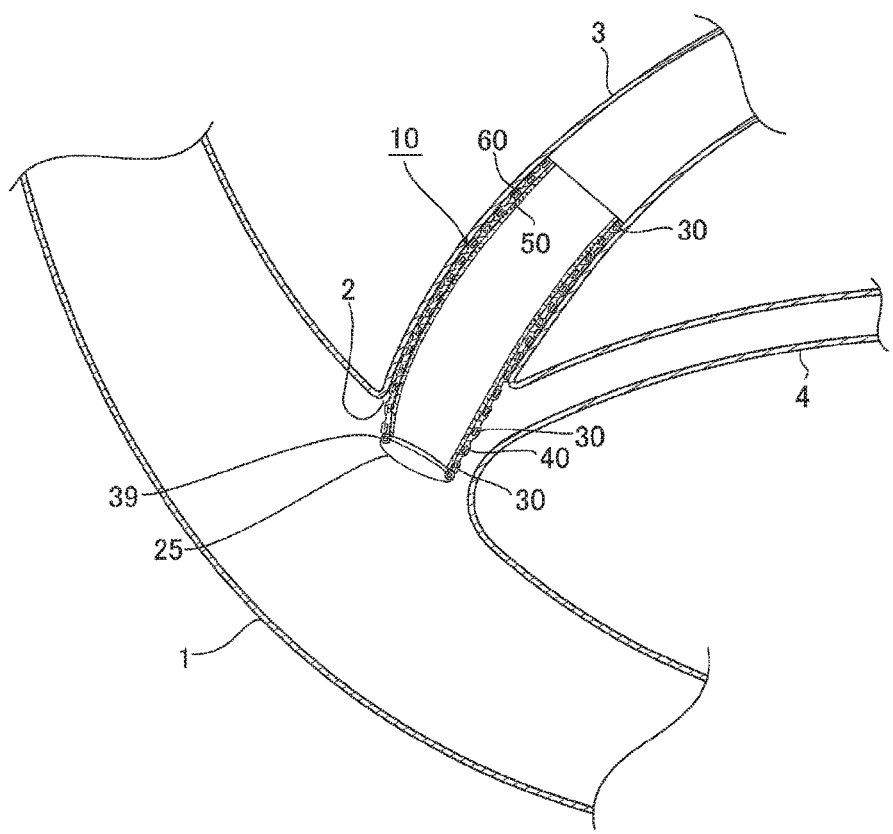
FIG. 6 is a diagram showing a state where the stent is indwelled in the body.

As shown in FIG. 6, the papilla 2 is disposed in a lower portion of the duodenum 1, and the bile duct 3 and the pancreatic duct 4 branch from the papilla 2 and extend. The bile produced in the liver which is not shown flows through the bile duct 3, passes through the papilla 2, and is then supplied to the duodenum 1. Here, the procedure of indwelling the stent 10 in the bile duct 3 via the papilla 2 will be described.

The stent 10 of the invention may be indwelled in, in place of the bile duct 3, a tubular organ such as the pancreatic duct 4, the esophagus, the trachea, the large intestine, or the blood vessel, a body cavity, or another body tissue. The application place is not particularly limited.

First, the diameter of the stent 10 is reduced, and the stent is housed in a medical tube which is not shown, such as a catheter or a sheath. In this case, the stent 10 in a reduced-diameter state is housed in the medical tube while directing the one end side of the stent in which the strut portion 30 having the pull-out portions 39 exists, toward the operator, and the other end side of the stent toward the tip end side of the tube.

After, in this state, a guide wire is inserted by a well-known method into the bile duct 3 through a lumen of an endoscope which is not shown, the medical tube is inserted via the guide wire, thereby inserting the stent 10 from the other end side into the bile duct 3. When a tip end portion of the medical tube then reaches a predetermined position of the bile duct 3, the insertion of the medical tube is ended. Thereafter, the stent 10 is released from the tube tip end via a pusher or the like, whereby the diameter of the stent 10 is reduced, and the stent 10 is indwelled so that, as shown in FIG. 6, the other end side of the stent is placed in the bile duct 3, and the one end side of the stent is placed so as to be slightly projected from the papilla 2.

In this way, the bile duct 3 is maintained in the increased diameter state by the stent 10 which is indwelled in the bile duct 3. In a case where the inner cavity of the stent 10 is closed by body fluid such as the bile, or growth of cancer cells, or where the treatment is ended, there may arise a case where the stent 10 is to be recovered from the body.

Figure 7:
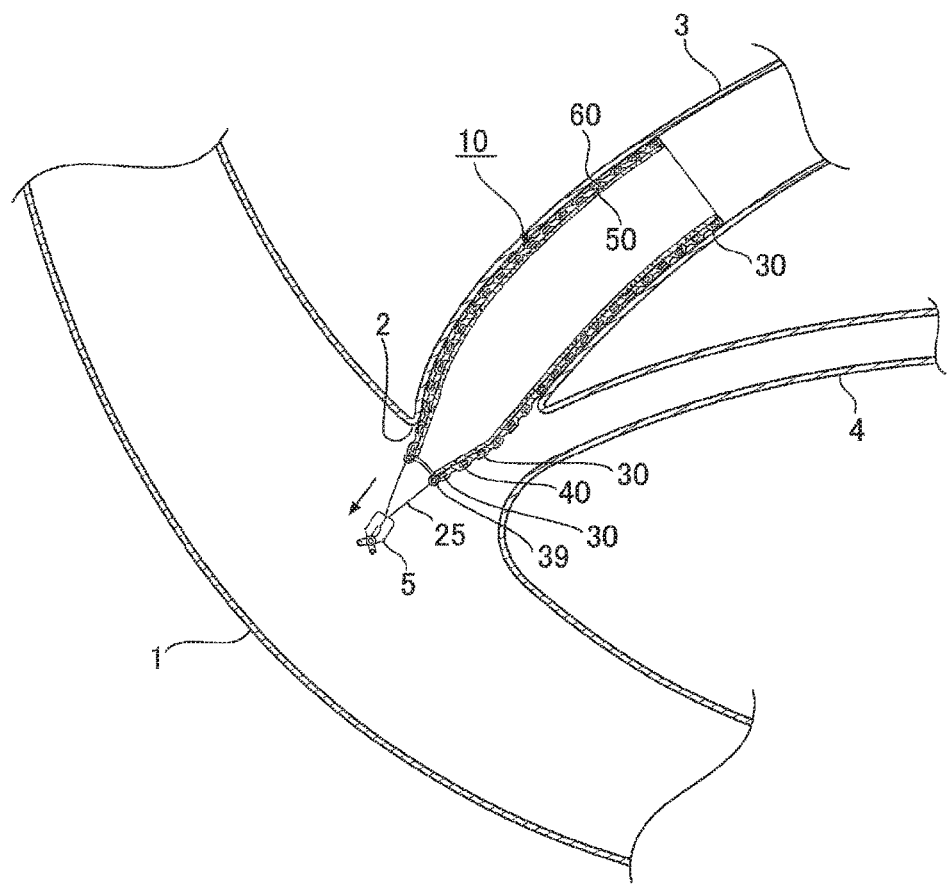
FIG. 7 is a diagram showing a state where the stent is pulled out from the body.

In this case, as shown in FIG. 7, the forceps 5 is inserted into the duodenum 1 through, for example, a lumen of an endoscope which is not shown, the loop-like pull-out wire 25 which is disposed on the one end side of the stent is gripped by the forceps 5, and, as shown in FIG. 5, the forceps 5 is pulled toward the operator. Alternatively, the one end side of the stent may be hooked by a loop-like snare, and the stent may be pulled via the snare. The means for pulling the stent is not particularly limited.

In this case, the structure is formed where each group of plural mountain portions 35 of the strut portions 30 other than the strut portion 30 which is positioned in the top on the one end side of the stent 10 and which has the pull-out portions 39 are bundled by each bridge portion 40, and coupled to the valley portion 37 of the strut portion 30 which is adjacent on the one end side of the stent, and all of the mountain portions 35 of the strut portions 30 other than the strut portion 30 which is positioned in the top on the one end side of the stent 10 and which has the pull-out portions 39 are coupled to the bridge portions 40. When the one end side of the stent is pulled as described above, therefore, all of the mountain portions 35 of the strut portions 30 other than the strut portion 30 which is positioned in the top on the one end side of the stent 10 and which has the pull-out portions 39 are pulled via the bridge portions 40 each of which bundles the plural mountain portions 35.

As a result, as shown in FIG. 5, the mountain portions 35 of the strut portions 30 are easily converged to reduce the diameter of the stent 10. Since all of the mountain portions 35 of the strut portions 30 other than the strut portion 30 which is positioned in the top on the one end side of the stent 10 and which has the pull-out portions 39 are coupled to the bridge portions 40, a bent portion which is projected from the one end side of the stent 10 does not independently exist. Therefore, the plural mountain portions 35 are hardly caught by the inner wall of the bile duct 3, so that the stent 10 can be smoothly extracted from a tubular organ such as the bile duct 3, a body cavity, or another body tissue. In the embodiment, the stent 10 which is extracted from the bile duct 3 can be recovered from the body through the lumen of the endoscope which is not shown.

The valley portions 37 of the strut portions 30 include those which are not coupled to the bridge portions 40, and therefore the spaces S surrounded by the bridge portions 40 and the strut portions 30 can be ensured to be wide. Consequently, the flexibility of the stent 10 can be enhanced, and, in a case such as that where the stent 10 is indwelled and bent in a curved tubular organ, or that where the stent 10 is compressed and bent by growth of cancer cells or the like, the stent 10 can be caused to hardly kink.

In the embodiment, since, as shown in FIGS. 3 and 4, each 3 mountain portions 35 of the strut portions 30 other than the strut portion 30 which is positioned in the top on the one end side of the stent 10 and which has the pull-out portions 39 are bundled by each bridge portion 40, and coupled to the valley portion 37 of the strut portion 30 which is adjacent on the one end side, moreover, the spaces S surrounded by the strut portions 30 and the bridge portions 40 can be made wider, and the stent 10 can be enhanced in flexibility, and caused to more hardly kink. Also, as shown in FIG. 8, each 4 mountain portions 35 of the strut portions 30 other than the strut portion 30 which is positioned in the top on the one end side of the stent 10 and which has the pull-out portions 39 can be bundled by each bridge portion 40, and coupled to the valley portion 37 of the strut portion 30 which is adjacent on the one end side. Also in this case, similar effects are achieved.

In the embodiment, since, as shown in FIGS. 3 and 4, the bridge portions 40 that are coupled to the mountain portions 35 of the strut portions 30 other than the strut portion 30 which is positioned in the top on the one end side of the stent 10 and which has the pull-out portions 39 are coupled to the valley portions 37 of the strut portions 30 which are adjacent on one end side, the wire members (the frames 31 and the frames 41) of the strut portions 30 and the bridge portions 40 can be suppressed from being placed concentrically in the circumferential direction, and the stent 10 can be caused to be easily bent, and hardly kink.

By arranging the valley portions 37 of each strut portion 30 such hat predetermined numbers (in the embodiment, 2) of valley portions which are not coupled to the bridge portions 40 exist in the circumferential direction between the valley portions which are coupled to the bridge portions 40, the flexibility in the case where the stent 10 is to be bent can be uniformly obtained. In addition, even when the stent 10 is bent in any direction, the stent hardly kinks.

Also the expandability in the case where the stent 10 is to be expanded from the reduced diameter state is uniformly ensured, and the stent can be indwelled in a balanced and uniform manner with respect to the inner wall of a tubular organ such as the bile duct 3, or another body tissue. Also the contractile force in the case where the diameter of the stent 10 in the increased diameter state is to be reduced is uniform, and the workability in diameter reduction can be enhanced.

Figure 11:
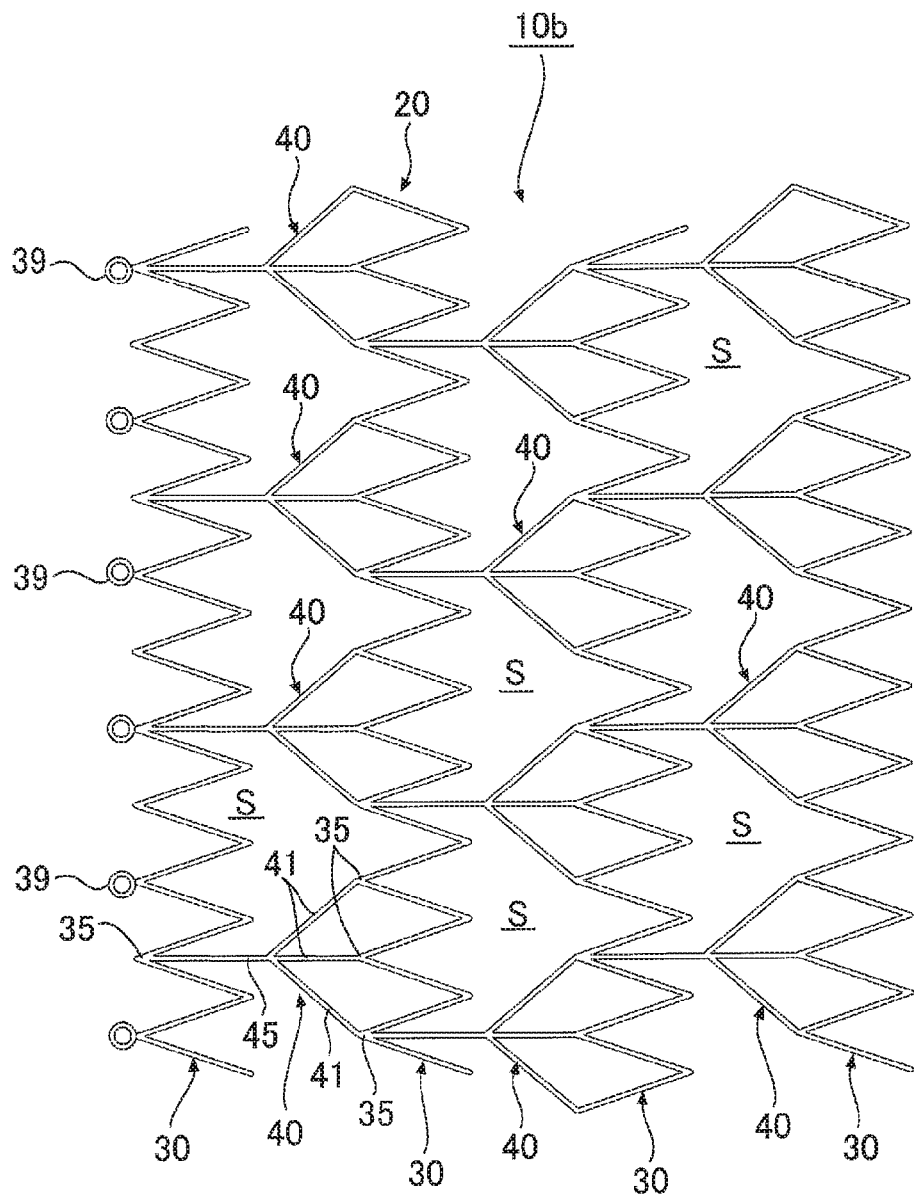
FIG. 11 shows a third embodiment of the stent of the invention, and is a development view of the stent main body constituting the stent.

As in a stent 10*b* of the third embodiment shown in FIG. 11, the mountain portions 35 of each strut portion 30 can be arranged such that predetermined numbers of mountain portions which are not coupled to the bridge portions 40 exist in the circumferential direction between the mountain portions that are coupled to the bridge portions 40. Also in this case, similar effects are achieved.

By arranging 3 to 5 (in the embodiment, 4) bridge portions 40 that bundle respectively pluralities of mountain portions 35 of the strut portions 30 other than the strut portion 30 which is positioned in the top on the one end side of the stent 10 and which has the pull-out portions 39, and that are coupled to the valley portions 37 or mountain portions 35 of the strut portions 30 which are adjacent on one end side are disposed in the circumferential direction of each strut portion 30, the spaces S between the strut portions 30 and the bridge portions 40 can be ensured to be wide. Therefore, the flexibility of the stent 10 can be enhanced, and the kink resistance can be further improved.

Figure 10:
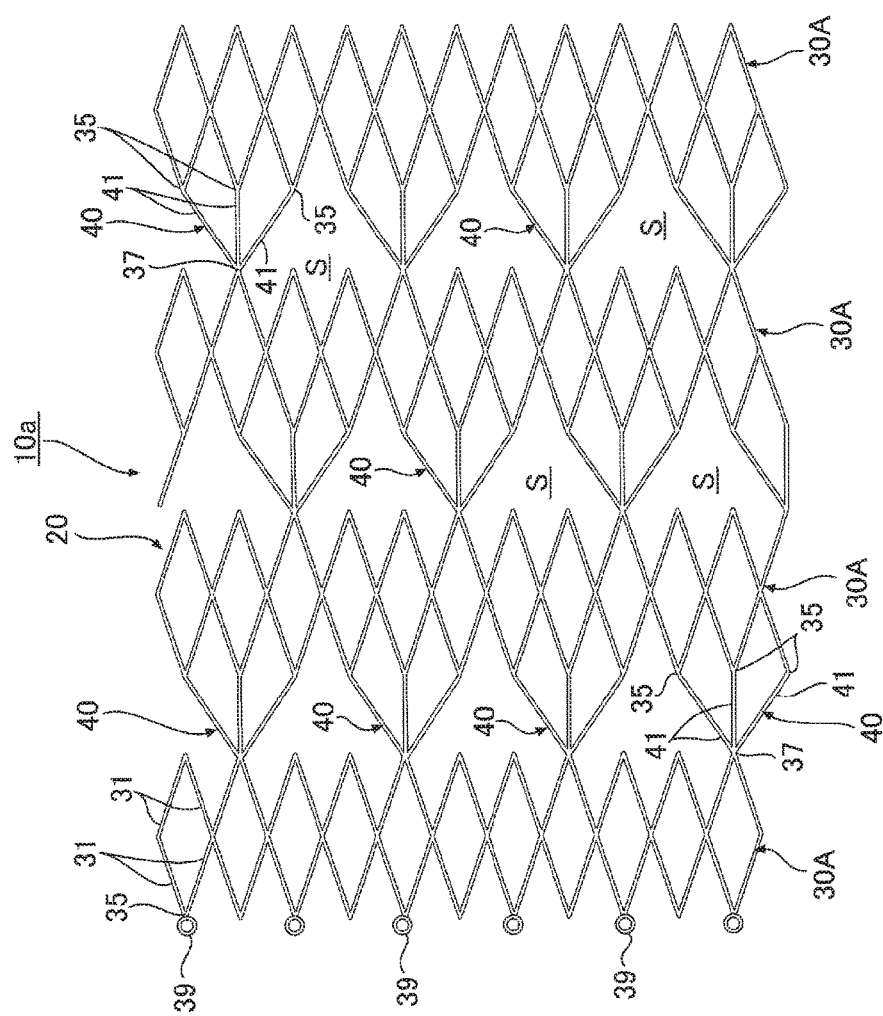
FIG. 10 shows a second embodiment of the stent of the invention, and is a development view of the stent main body constituting the stent.

FIG. 10 shows the second embodiment of the stent of the invention. The components which are substantially identical with those of the above-described embodiment are denoted by the same reference numerals, and their description is omitted.

The stent 10 of the first embodiment has the zig-zag shaped strut portions 30. As shown in FIG. 10, by contrast, the stent 10*a* of the present embodiment has a structure in which each strut portion 30A is annularly formed by coupling plural frame-like members having a predetermined bent shape, to one another in juxtaposition in a circumferential direction of the stent.

The frame-like members in the embodiment have a substantially rhombic shape which is long in the axial direction of the stent, and short in the circumferential direction of the stent. Alternatively, for example, the frame-like members may have a substantially hexagonal shape similar to a turtle shell, a substantially spindle-like shape in which the both ends are edged, or another shape. The shape of the frame-like members is not particularly limited as far as each member has the mountain portion 35 and the valley portion 37, and exhibits a frame-like shape.

Also in the stent 10*a* of the embodiment, similar effects as those of the stent 10 of the first embodiment are achieved.

FIG. 11 shows the third embodiment of the stent of the invention. The components which are substantially identical with those of the above-described embodiments are denoted by the same reference numerals, and their description is omitted.

As shown in FIG. 11, the stent 10*b* of the embodiment has a structure in which 3 frames 41 constituting the bridge portion 40 are coupled respectively to 3 mountain portions 35 of each strut portion 30 other than the strut portion 30 which is positioned in the top on the one end side of the stent 10*b* and which has the pull-out portions 39, the 3 frames 41 are bundled together into one portion at a middle position on the way toward the one end side of the stent, and the bundled portion 45 is coupled to the mountain portion 35 of the strut portion 30 which is adjacent on the one end side.

In the stent 10*b* of the embodiment, since the bridge portions 40 that are coupled to the mountain portions 35 of each strut portion 30 other than the strut portion 30 which is positioned in the top on the one end side of the stent 10*b* and which has the pull-out portions 39 are bundled together into one portion at a middle position, and the bundled portion 45 which is formed into one portion by bundling is coupled to the mountain portion 35 of the strut portion 30 which is adjacent on the one end side, the spaces S surrounded by the strut portions 30 and the bridge portions 40 can be ensured to be wide, and therefore the flexibility of the stent 10*b* can be further enhanced.

Figure 12:
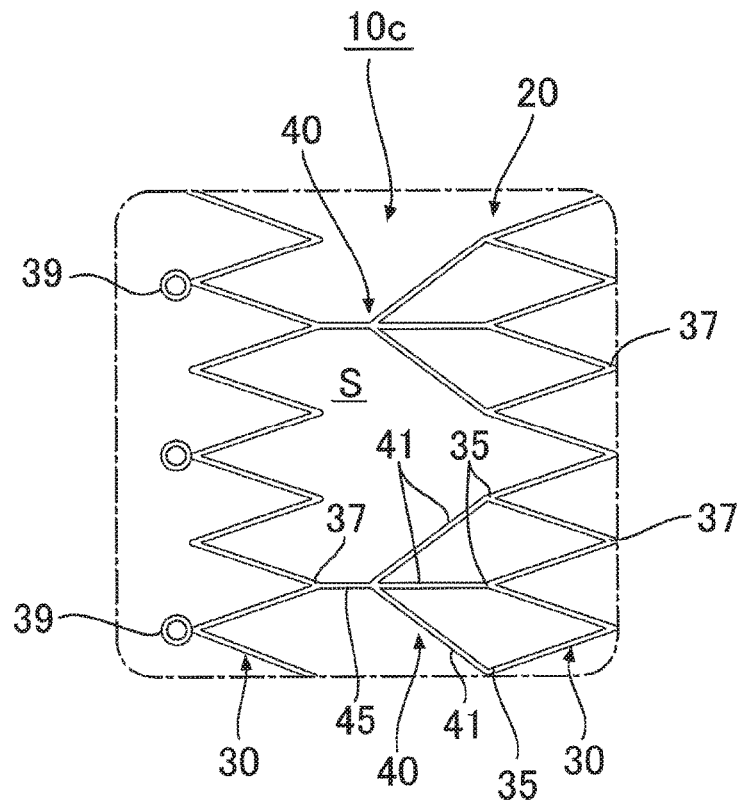
FIG. 12 shows a fourth embodiment of the stent of the invention, and is an enlarged development view of main portions of the stent main body constituting the stent.

FIG. 12 shows a fourth embodiment of the stent of the invention. The components which are substantially identical with those of the above-described embodiments are denoted by the same reference numerals, and their description is omitted.

As shown in FIG. 12, similarly with the stent 10b of the third embodiment, the stent 10c of the present embodiment has a structure in which the middles of the bridge portions 40 are bundled into one portion, and the bundled portion 45 is coupled to the valley portion 37 of the strut portion 30 which is adjacent on the one end side.

The stent 10c of the embodiment achieves similar effects as the stents 10, 10b of the first and third embodiments.

Figure 13:
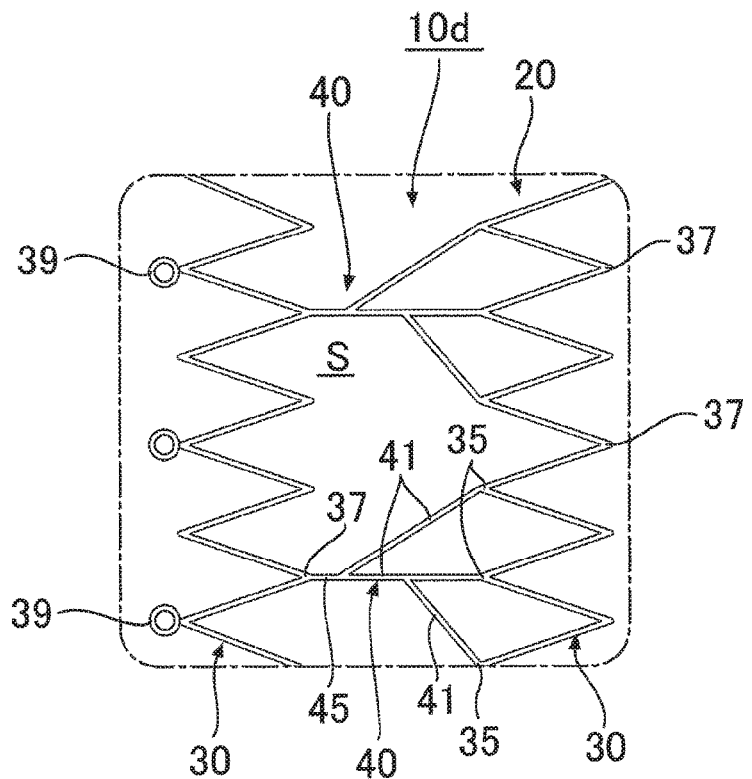
FIG. 13 shows a fifth embodiment of the stent of the invention, and is an enlarged development view of main portions of the stent main body constituting the stent.

FIG. 13 shows a fifth embodiment of the stent of the invention. The components which are substantially identical with those of the above-described embodiments are denoted by the same reference numerals, and their description is omitted.

As shown in FIG. 13, the stent 10d of the embodiment has a structure in which groups of 3 frames 41 constituting the bridge portion 40 are coupled respectively to groups of 3 mountain portions 35 of the strut portions 30 other than the strut portion 30 which is positioned in the top on the one end side of the stent 10d and which has the pull-out portions 39, the 3 frames 41 are sequentially bundled into one member at respective middle positions on the way toward the one end side of the stent while being shifted from one another in the axial direction, and the bundled portion 45 which is formed into one portion by bundling is coupled to the valley portion 37 of the strut portion 30 which is adjacent on the one end side.

Although, in each bridge portion 40 in the embodiment, the other end side (the basal end side of each frame) is coupled to 3 mountain portions 35, the bridge portion may be coupled to 3 or more mountain portions 35.

In the stent 10d of the embodiment, in each bridge portion 40 that is coupled to 3 or more mountain portions 35 of each strut portion 30 other than the strut portion 30 which is positioned in the top on the one end side of the stent 10d and which has the pull-out portions 39, the frames are sequentially bundled into one member at respective middle position on the way toward the one end side while being shifted from one another in the axial direction. When the diameter of the stent 10d in the increased diameter state is to be reduced, therefore, the frames 41 of each bridge portion 40 that is coupled to 3 or more mountain portions 35 are sequentially folded down to reduce the diameter, and hence the diameter of the stent 10 can be easily reduced. In a configuration where plural bridge portions 40 are bundled at one position, stress is concentrated in a folding process, and therefore the diameter of a stent is hardly reduced.

The invention is not limited to the above-described embodiments. Various modified embodiments can be made without departing from the spirit of the invention, and such embodiments are included within the scope of the invention.

REFERENCE SIGNS LIST 10, 10a, 10b, 10c, 10d stent
20 stent main body
30, 30A strut portion
32 space
35 mountain portion
37 valley portion
40 bridge portion
45 bundled portion

The invention claimed is:

1. A stent having a distal end and a proximal end, the stent, including:

plural strut portions, each of which is formed from a single-continuous annular strut bent in a zigzag pattern and coupled at both ends of said each strut portions to have an annular shape; and plural bridge portions which couple together the plural strut portions in an axial direction, wherein all the bridge portions are each formed by 3 or 4 frames coupled together, wherein said each strut portion includes:
   mountain portions which correspond to bent portions that are projected toward the distal end of the stent, the mountain portions comprising V-shape bent portions that project distally; and
   valley portions which correspond to bent portions that are projected toward the proximal end of the stent, the valley portions comprising V-shape bent portions that project proximally, wherein the V-shape bent portions of the mountain portions are directly connected by straight frames to the V-shape bent portions of the valley portions, wherein all the mountain portions of said each strut portion, other than the strut portion which is positioned at the distal end, are coupled to the bridge portions, are bundled into groups of 3 or 4 mountain portions by the bridge portions, and are coupled to the valley portions of another strut portion which is distally adjacent, and wherein a part of the valley portions of said each strut portion is not coupled to the bridge portions.

2. The stent of claim 1, wherein the bridge portions, which are coupled to the 3 or 4 mountain portions of said each strut portion other than the strut portion which is positioned at the distal end, are coupled to the valley portions of the another strut portion which is adjacent distally.

3. The stent of claim 1, wherein the bridge portions, which are coupled to the 3 or 4 mountain portions of said each strut portion other than the strut portion which is positioned at the distal end, are each bundled such that the plural mountain portions are bundled into a bundled portion at a position between said each strut portion and the another strut portion, and
   wherein the bundled portion is coupled to the valley portion or the mountain portion of the another strut portion which is adjacent distally.

4. The stent of claim 1, wherein the valley portions of said each strut portion, other than the strut portion which is positioned at the distal end, include a constant number of the valley portions which are not coupled to the bridge portions in a circumferential direction between the valley portions or the mountain portions which are coupled to the bridge portions.

5. The stent of claim 1, wherein, with said each strut portion, other than the strut portion which is positioned at the distal end, 3 to 6 bridge portions are disposed in a circumferential direction, the 3 to 6 bridge portions being coupled to the 3 or 4 mountain portions.

6. The stent of claim 1, wherein the bridge portions, which are coupled to the 3 or 4 mountain portions of said each strut portion other than the strut portion which is positioned at the distal end, are each bundled such that the mountain portions are sequentially bundled at respective positions toward the distal end while being shifted from one another in the axial direction into a bundled portion, and
   wherein the bundled portion is coupled to the valley portion or the mountain portion of the another strut portion which is adjacent distally.

7. The stein of claim 1, wherein each of the 3 or 4 frames of said each bridge portions extends in a straight line from the mountain portions to the valley portions.

8. The stent of claim 1, wherein a tip of the V-shape bent portions of the mountain portions is connected to a tip of the V-shape bent portion of corresponding valley portions.

9. The stent of claim 1, wherein a tip of the V-shape bent portions of the mountain portions is directly connected to a tip of the V-shape bent portion of corresponding valley portions.

10. The stent of claim 1, wherein the straight frames directly connect a tip of the V-shape bent portions of the mountain portions to a tip of the V-shape bent portion of corresponding valley portions.

* * * * *